US010820987B2

(12) United States Patent
Basinger et al.

(10) Patent No.: US 10,820,987 B2
(45) Date of Patent: **\*Nov. 3, 2020**

(54) INTRAOCULAR DEVICE WITH WIRELESSLY COUPLED AUXILIARY ELECTRONICS

(71) Applicant: Verily Life Sciences LLC, Mountain View, CA (US)

(72) Inventors: Brooke C. Basinger, San Jose, CA (US); Dimitri Azar, Chicago, IL (US); Jeremy Emken, San Jose, CA (US); Anil Ram Rakhyani, San Jose, CA (US); Patricia E. Johnson, San Carlos, CA (US); Daniel B. Otts, San Carlos, CA (US); Sohyun Park, Santa Clara, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/107,561

(22) Filed: Aug. 21, 2018

(65) Prior Publication Data

US 2019/0000611 A1 Jan. 3, 2019

Related U.S. Application Data

(63) Continuation of application No. 15/194,245, filed on Jun. 27, 2016, now Pat. No. 10,076,408.

(51) Int. Cl.
*A61F 2/16* (2006.01)
(52) U.S. Cl.
CPC .......... *A61F 2/1624* (2013.01); *A61F 2/1613* (2013.01); *A61F 2/1635* (2013.01);
(Continued)

(58) Field of Classification Search
CPC ............ A61F 2/1624; A61F 2250/0001; A61F 2250/0002
See application file for complete search history.

(56) References Cited

U.S. PATENT DOCUMENTS 7,857,850 B2 12/2010 Mentak et al.
8,778,022 B2 7/2014 Blum et al.
(Continued)

FOREIGN PATENT DOCUMENTS

CN 102026680 A 4/2011
CN 104582635 A 4/2015
(Continued)

OTHER PUBLICATIONS

PCT/US2017/031701—International Search Report and Written Opinion of the International Searching Authority, dated Aug. 18, 2017, 16 pages.
(Continued)

*Primary Examiner* — David H Willse
*Assistant Examiner* — Javier G Blanco
(74) *Attorney, Agent, or Firm* — Christensen O'Connor Johnson Kindness PLLC

(57) ABSTRACT

Techniques and mechanisms for the wireless transmission of power and sensor information between two components of an implantable ophthalmic device are disclosed herein. An example device includes an accommodating intraocular lens (aIOL) and separate auxiliary electronics, both enclosed in biocompatible materials. The aIOL includes a dynamic optic, control logic, a battery and an antenna. The auxiliary electronics include an antenna, an energy storage cell, and a sensor. The auxiliary electronics may be wirelessly coupled to the aIOL for the wireless transmission of power and sensor information.

10 Claims, 5 Drawing Sheets

(52) U.S. Cl.
CPC ............... *A61F 2250/0001* (2013.01); *A61F 2250/0002* (2013.01); *A61F 2250/0069* (2013.01)

(56) References Cited

U.S. PATENT DOCUMENTS

| | | | |
|---|---|---|---|
| 2007/0260307 A1 | 11/2007 | Azar | |
| 2008/0021549 A1* | 1/2008 | Eagan | A61F 2/1616 623/6.22 |
| 2009/0264966 A1* | 10/2009 | Blum | A61N 1/36046 607/61 |
| 2011/0248671 A1 | 10/2011 | Dos Santos et al. | |
| 2012/0226132 A1 | 9/2012 | Wong et al. | |
| 2013/0184815 A1 | 7/2013 | Roholt | |
| 2013/0282117 A1 | 10/2013 | Van Heugten et al. | |
| 2014/0058506 A1* | 2/2014 | Tai | A61N 1/0543 623/4.1 |
| 2015/0173893 A1 | 6/2015 | Portney | |

FOREIGN PATENT DOCUMENTS

| | | | |
|---|---|---|---|
| WO | 2006015315 A2 | 2/2006 | |
| WO | WO-2006015315 A2 * | 2/2006 | ........... G02B 27/017 |
| WO | 2007/107589 A1 | 9/2007 | |
| WO | 2015/105881 A1 | 7/2015 | |
| WO | 2015/138507 A1 | 9/2015 | |

OTHER PUBLICATIONS

Chinese Office Action, with English Translation, dated Mar. 5, 2020, in corresponding Chinese Patent Application No. 2017800400966, 37 pages.

European Extended Search Report, dated Jun. 30, 2020, in corresponding European Patent Application No. 20165156.9, 8 pages.

* cited by examiner

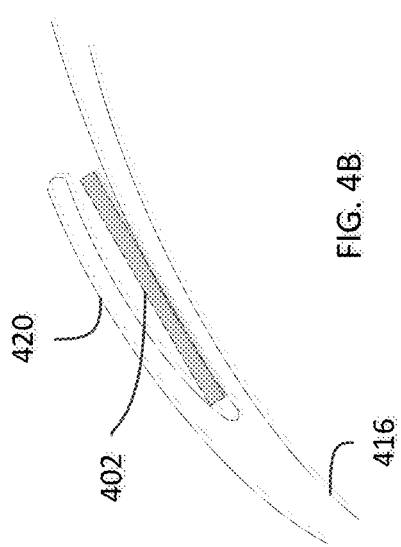
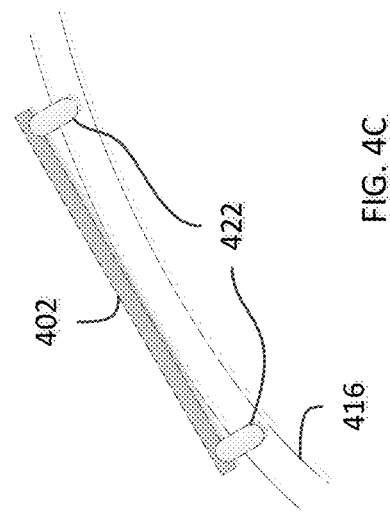
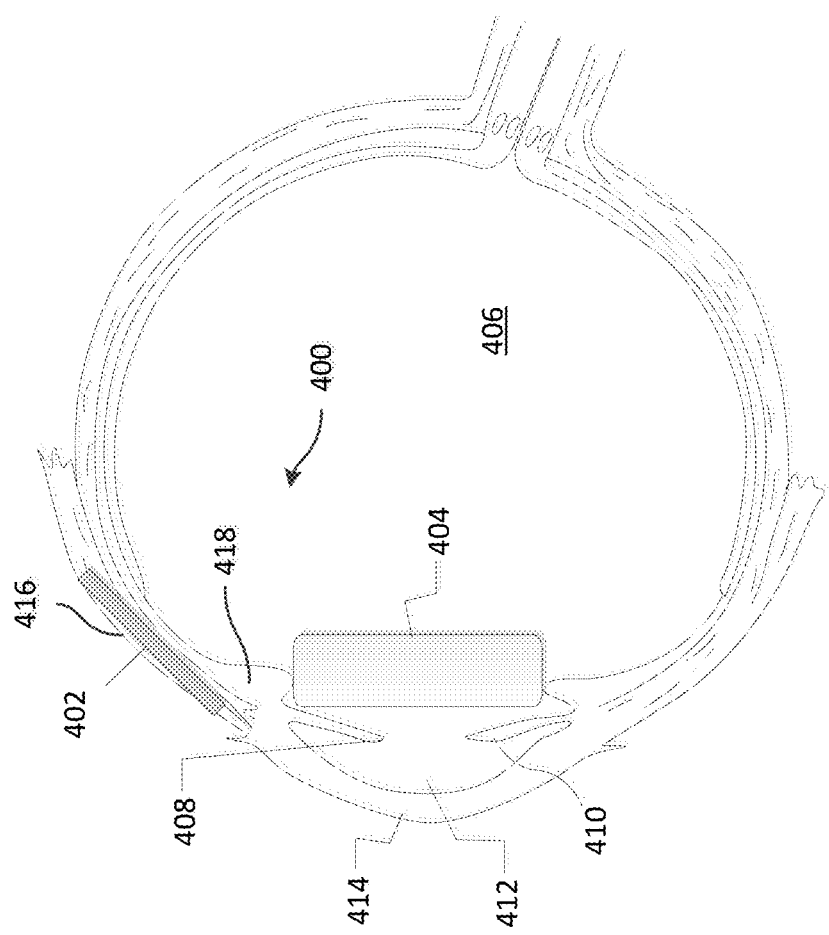

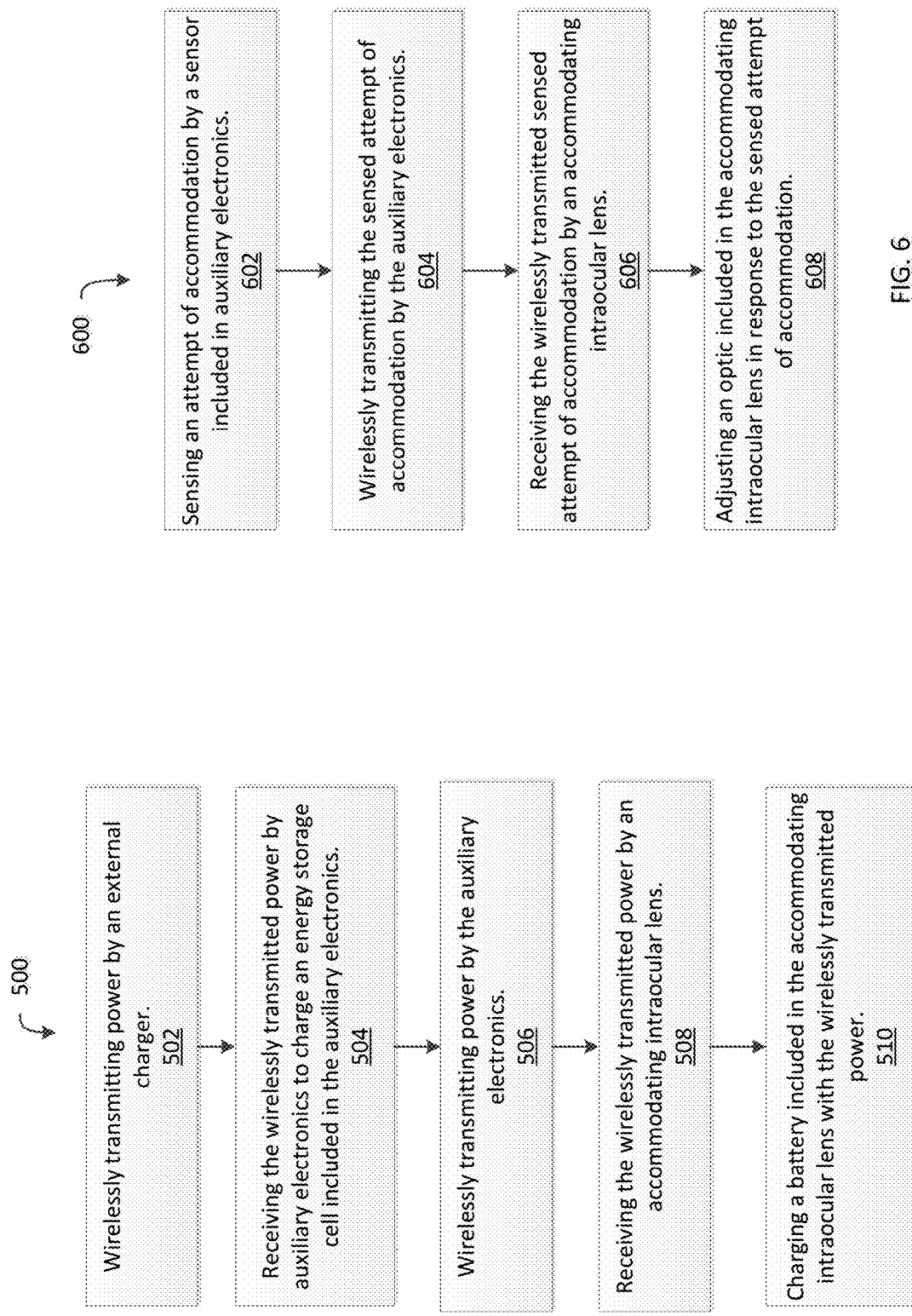

INTRAOCULAR DEVICE WITH WIRELESSLY COUPLED AUXILIARY ELECTRONICS

CROSS-REFERENCE TO RELATED APPLICATION

This application is a continuation application of U.S. patent application Ser. No. 15/194,245, filed on Jun. 27, 2016, the contents of which are incorporated herein by reference.

TECHNICAL FIELD

This disclosure relates generally to implantable ophthalmic devices, and in particular but not exclusively, relates to wirelessly coupled components of an intraocular device.

BACKGROUND

Accommodation is a process by which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and, when contracted, relieves tension applied to the lens via the zonules, causing the lens to relax, change shape, and thus alter its optical power.

As an individual ages, accommodation degrades due to physiological changes in the lens and surrounding tissues. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages.

Recent technologies have begun to provide for various devices that operate in or on a human eye to aid the visual focus of a user. Devices intended to aid in accommodation may take the form of an intraocular lens (IOL), contact lens, or corneal inlay. An electro-active accommodating lens in any of these configurations may include one or more elements and circuitry to apply an electrical signal to change a focusing power of the one or more elements. As successive generations of integrated circuitry continue to scale down in size and power consumption, there is expected to be an increased demand for additional functionality to be incorporated in medical devices such as accommodation-capable (or other) ophthalmic implants. Meeting this demand is constrained by the size of the human eye, which limits the amount of space available for an intraocular device to provide communication, sensor, power and/or other functionality.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 4A is a cross-sectional illustration of an eye with an implanted ophthalmic device including wirelessly coupled structures in accordance with one embodiment of the present disclosure.

FIG. 4B is a cross-sectional view of a portion of an eye with an implantable auxiliary electronic in accordance with an embodiment of the present disclosure.

FIG. 4C cross-sectional view of a portion of an eye with an implantable auxiliary electronic in accordance with an embodiment of the present disclosure.

FIG. 5 is an example method for wirelessly transmitting power from implanted auxiliary electronics to an implanted aIOL in accordance with an embodiment of the present disclosure.

FIG. 6 is an example method for wirelessly transmitting sensor information from implanted auxiliary electronics to an implanted aIOL in accordance with the present disclosure.

DETAILED DESCRIPTION

Figure 1:
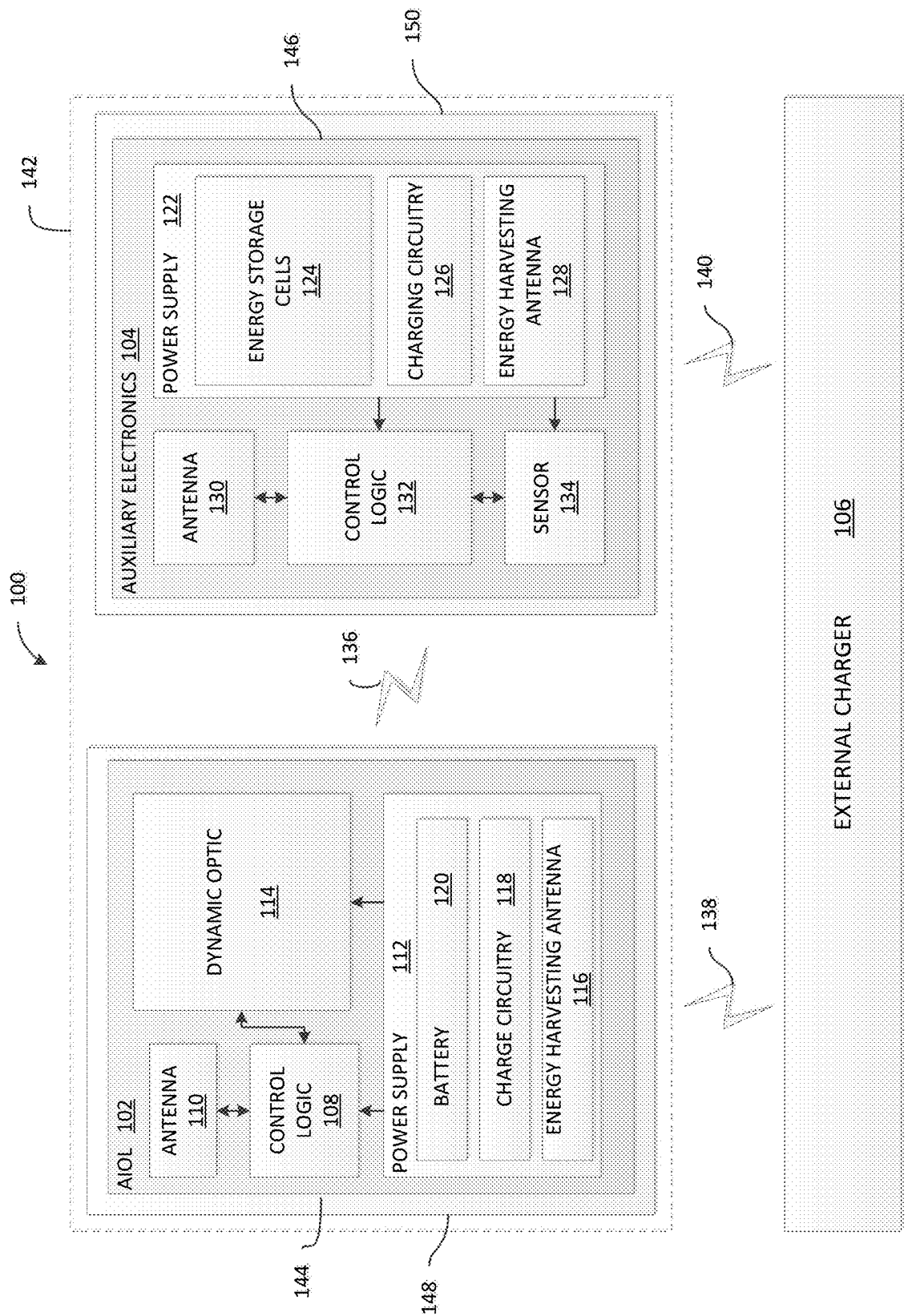
FIG. 1 is a block diagram of an ophthalmic lens system in accordance with an embodiment of the present disclosure.

Embodiments described herein variously provide for an implantable ophthalmic device that includes wirelessly coupled sections, such as an intraocular lens and auxiliary electronics. Rather than encasing all components in a single vessel, implantable ophthalmic devices according to some embodiments variously distribute components across multiple sections that are wirelessly coupled to one another. Such sections may be wirelessly coupled to one another via one or more antennae. The sections may, for example, both be disposed in a biocompatible material. The antennae may include, for example, conductors formed into helical coils and embedded in medical grade silicone and/or flex circuits fabricated from biocompatible materials. Providing wireless coupling between the sections, each section may be implanted in a different area of the eye based on the respective function of the section and the space needed for implantation. Additionally, by providing two or more physically separated sections, incisions made for the respective implantable sections may be reduced in size comparable to the incision required for a monolithic device.

Certain features of various embodiments are described herein with reference to an ophthalmic device that provides different levels of accommodation to aid sight with an eye. However, some embodiments are not limited to the providing of automatic accommodation, and such description may be extended to additionally or alternatively apply to any of a variety of other implantable ophthalmic devices. For example, a device according to another embodiment may provide only one level of accommodation. In another embodiment, an implantable device includes one or more sensors to detect a condition (e.g., a level of intraocular pressure) in or on the eye—e.g., in addition to, or in lieu of, the device aiding sight by the eye. In another embodiment, an implantable device includes reversible chemical assays to assess analyte concentrations.

Ophthalmic devices discussed herein may comprise multiple portions or segments, referred to herein as "components", that are coupled to one another via one or more antennae, e.g., they are wirelessly coupled. Wireless coupling may allow for the different components to be placed in different eye locations, which may ultimately ease the surgery for placement and/or replacement of both. Each component may be at least a semi-rigid structure that are enclosed in a biocompatible material. Such components may include circuitry, optics, one or more sensors and/or the like. An enclosure may hermetically seal some or all such components.

An exterior of an ophthalmic device according to one embodiment may include respective surfaces of multiple components. Such surfaces may be formed by one or more biocompatible materials that accommodate implantation of the ophthalmic device in a human (or other) eye. Examples of some biocompatible materials that may be used include, but are not limited to, any of various biocompatible hydrogels, silicones, hydrophobic acrylics, fluorinated polymethacrylates and/or the like. In an embodiment, one or more components include a coating of biocompatible material that, for example, is formed by atomic layer deposition. Such materials may be adapted from those used in existing intraocular devices, for example.

In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Accommodating intraocular lenses (aIOLs) available today may be mechanically actuated. For example, a mechanical component of an aIOL may be actuated by eye muscles and connected tissues, such as the ciliary muscle, ciliary processes and ciliary bag, to cause the aIOL to accommodate, e.g., change focus. For example, the actuation may cause an optic of the aIOL to adjust an optical strength commensurate with the muscular change of the eye muscles. The general intent of the aIOL being to replicate the natural focusing of the eye using implanted lenses. These mechanically actuated aIOLs, however, do not replicate natural focusing well due to compromised integrity of the natural mechanical system in the eye, which may limit the level of accommodation provided by the aIOL.

Electronically controlled aIOLs, may provide more consistent accommodation results across patients. Electronically controlled aIOLs, however, require a power source to operate the electronics and the actuation of the optic, among other things. While integration of the power source and the aIOL may be desired, the volume of the eye available for placement of the aIOL and the incision size that can be tolerated in various locations are limited, which constrains the size of the aIOL. A size-limited aIOL may, in turn, limit the battery size and a battery lifetime. Although the electronics and the actuators may operate at low powers, the longevity and the size of the battery is of concern. If the longevity of the battery is limited, the battery may require periodic replacement, every 5 to 10 years for example. As such, if the battery is integrated with the aIOL, then the entire aIOL may need to be replaced in order to replace the battery. Replacement, as one would understand, would require additional surgery, which may involve incisions in delicate areas of the eye.

AIOLs, in general, may be located in the capsular bag, anterior chamber, or the sulcus, for example, which may affect the location of the power source. An additional complication to the placement of the power source may be due to the connection required between it and the aIOL. For example, if the connection is physical, e.g., a wire, additional incisions may be required and the location of the power source may need to be close to the aIOL. As such, if the aIOL is implanted in the anterior chamber, then the power source may also need to be similarly located, which may negatively affect the size of the power source. As such, the invasiveness of the initial surgery and a battery replacement surgery may be reduced if at least a power source for the aIOL is physically separate from the aIOL (e.g., not tethered by a physical connection), and implanted in a more accessible region of the eye.

Additionally, for the aIOL to operate as intended, a sensor or sensor network may also be implanted in the eye to determine when and how much to accommodate. The sensor, which may use more power than the other aIOL electronics in some instances, may also affect the size of the power source. One technique to determine when and how much to accommodate may be to use a sensor capable of performing electromyography (EMG) on the muscles that control focusing, e.g., the ciliary muscle. The sensor may measure the EMG of the ciliary, e.g., ciliary EMG, to determine a patient's intent to accommodate. The ciliary EMG information may be correlated with a change in focus, which may be used to determine an amount of accommodation to apply to the optic of the aIOL. The aIOL, due to implant location, may not have simple access to the ciliary muscle, which may require the sensor to be placed in a location different than the aIOL.

Accordingly, faced with the above constraints, it may be desirable to have a power source implanted in a more easily accessible location of the eye, and in a location that allows for a larger power source implant. Further, to overcome the interconnection concern between the aIOL and the power source, the power source may wirelessly deliver power to the aIOL. As a result, the aIOL may be wirelessly charged, and a physical connection between the two may be omitted. The power source may also be wirelessly charged, such as by an external charging device. Further, a sensor may accompany the power source and wirelessly provide sensor data to the aIOL. In one example, the sensor may detect ciliary muscle EMG to determine an eye's intent to accommodate. Alternatively or additionally, the sensor may also detect and utilize strains, forces, deflections in the aIOL or surrounding tissue to determine an eye's intent to accommodate.

By wirelessly providing power and sensor data to the aIOL, the combination of a power source and a sensor, which may be referred to herein as "auxiliary electronics," may be placed in an area of the eye capable of holding a larger implant. In some embodiments, the auxiliary electronics implant may be anchored to or partially covered by the sclera. Because the sclera may accommodate a larger implant than the anterior chamber, for example, the auxiliary electronics implant may be less size-limited, which may allow for a larger power source. A larger power source, in turn, may allow for longer battery life, which may lead to fewer or no replacement surgeries. Additionally, in the event the power source needs replacement, the sclera location may make the replacement surgery less invasive.

Surgical procedures similar to a trabeculectomy, which are performed to relieve eye pressure for glaucoma patients, may be used to implant the power source/sensor in a user's eye. For example, the auxiliary electronics may be anchored to or partially implanted in the sclera. For example, a flap may be created in the sclera (without piercing the anterior chamber) and the auxiliary electronics may be placed within the flap. Alternatively or additionally, the auxiliary electronics may be anchored to the sclera using anchoring tabs. Locating the power source in or on the sclera may provide several advantages, such as being surgically accessible using a known procedure (e.g., no new surgical techniques are required), a reasonably large area is available that is reasonably close to the proposed aIOL location in the capsular bag or sulcus, and located very near the ciliary body, potentially providing a good location for monitoring ciliary activity as a means of detecting a patient's intent to accommodate.

In general, the present disclosure allows for electronically controlled aIOLs to have their optical components, and control mechanisms, to be placed into the optical path of the eye while bulkier non-optical components may be placed in a more accessible area of the eye, such as the sclera. Such placement allows for less invasive power source replacement surgery. Sclera placement of the power source may also increase the amount of volume available for the power source, which may allow for a higher capacity power source and a more robust and traditional hermetic enclosure. Additionally, separating a main power source from the aIOL optical components may allow for smaller incision sizes for placement of the aIOL optical components, which are made in more delicate regions of the eye. Moreover, providing access to the power source in the sclera may simplify power source replacement surgery, and avoids complications of intraocular surgery, such as additional incisions through the cornea, damage to the capsular bag, and movement of the aIOL, among other things.

FIG. 1 is a block diagram of an ophthalmic system 100 including a wirelessly coupled, implanted auxiliary component according to an embodiment of the present disclosure. In the illustrative embodiment shown, system 100 includes an implantable ophthalmic device 142 and an external charger 106. The implantable ophthalmic device 142, which includes an accommodating intraocular lens (aIOL) 102 and auxiliary electronics 104, may accommodate implantation in an eye, human or other, and perform sensing and aid to eyesight, e.g., accommodation. The aIOL 102 and the auxiliary electronics 104 may be implanted in different locations of an eye, whereas the external charger 106 is located outside of the eye. The aIOL 102, auxiliary electronics 104, and external charger 106 may be wirelessly coupled to one another via one or more antennae included in each. The System 100 may allow for wireless charging through inductive coupling, e.g., inductive charging, of the aIOL 102 and the auxiliary electronics 104. For example, the aIOL 102 may be inductively charged by the auxiliary electronics 104, which may have been inductively charged by the external charger 106. Additionally, the aIOL 102 may be inductively charged by the external charger 106.

The aIOL 102 may be capable of being implanted into an anterior chamber, posterior chamber, capsular bag, sulcus, or other location of a user's eye. The aIOL 102 is one example embodiment wherein components (e.g., including one or more of circuitry, optics, a battery, etc.) are disposed in an enclosure 148 that is formed from a biocompatible material, which may be a biocompatible enclosure. The biocompatible material or materials may seal respective components disposed therein, e.g., to provide protection for the interior of an eye in which aIOL 102 is to be implanted. Some enclosure material may be optically transmissive (e.g., transparent, clear, etc.), in an embodiment. For example, some or all of the enclosure material may be implemented as a silicon enclosure, or with any of other hermetically sealable materials. Of course, other optically transmissive and biocompatible materials may be used. In some embodiments, the aIOL 102 includes control logic 108, antenna 110, power supply 112, and a dynamic optic 114, all or some of which may be disposed on a surface of substrate 144.

The dynamic optic 114 may aid a user's eye sight using one or more lenses that include mechanisms capable of providing accommodation. Some examples of such mechanisms include liquid crystal, fluidic, electrowetting and/or the like. The dynamic optic, which may be part of or include in the enclosure 148, may provide an aperture region aligned with the user's cornea that provides the accommodation. In some embodiments, the dynamic optic 114 may provide accommodation in response to control signals provided by the control logic 108. In some embodiments, the control signals may originate in control logic 132 of the auxiliary electronics 104. In either embodiment, the control signals may be in response to attempted eye accommodation sensed by sensor 134 of the auxiliary electronics 104.

Control logic 108, in response to sensor data received from the auxiliary electronics 104, may determine a new level of accommodation to be provided by the dynamic optic 114. The new level of accommodation may be provided to the dynamic optic 114 via a wired or wireless electrical connection. Control logic 108 may include circuit logic that coordinates the operation of other components of aIOL 102, and may be implemented as hardware logic (e.g., application specific integrated circuit, field programmable gate array, etc.), software/firmware logic executed on a general purpose microcontroller, or a combination of both hardware and software/firmware logic.

Power supply 112 may be implemented using a variety of power storage devices including a rechargeable battery and/or capacitive elements, which may form battery 120. Charging circuitry 118, coupled to provide charging of battery 120, may include an inductive charging element, such as energy harvesting antenna 116.

Power supply 112 includes the battery 120 to power the various embedded electronics, including control logic 108 and dynamic optic 114. Battery 120 may be inductively charged by charging circuitry 118 and energy harvesting antenna 116. In one embodiment, antenna 110 and energy harvesting antenna 116 are independent antennae, which serve their respective functions of energy harvesting and communications. In another embodiment, energy harvesting antenna 116 and antenna 110 are the same physical antenna that provide respective functions for time-shared inductive charging and wireless communications with auxiliary electronics 104.

Charging circuitry 118 may include a rectifier/regulator to condition the captured energy for charging battery 120 or directly power control logic 108 without battery 120. Charging circuitry 118 may also include one or more energy storage devices to mitigate high frequency variations in energy harvesting antenna 116. For example, one or more energy storage devices (e.g., a capacitor, an inductor, etc.) may be connected to function as a low-pass filter.

The auxiliary electronics 104 may also be a device that lends itself to implantation into a user's eye. The auxiliary electronics 104 may be enclosed in enclosure 150, which may be a biocompatible material. The auxiliary electronics 104 may be implanted into the user's eye along with the aIOL 102, but the implant location may be different. For example, the aIOL 102 may be implanted in the anterior or posterior chamber, whereas the auxiliary electronics 104 may be (at least partially) implanted in or anchored to the sclera. Locating the auxiliary electronics 104 in the sclera may provide several benefits, such as a less invasive surgery if the auxiliary electronics require replacement, a larger area that allows for a larger power source, which may provide a longer battery life leading to fewer or no replacement surgeries. Additionally, the sclera location may allow a sensor, such as sensor 134, to detect an eye's attempts to accommodate by monitoring the ciliary muscle using EMG, pressure, temperature, strain or other biomarkers. The auxiliary electronics 104 may be wirelessly coupled to the aIOL 102 through wireless coupling 136 to inductively charge the battery 120 of the aIOL 102 and/or to wirelessly transmit data regarding the user's attempts to accommodate.

The illustrated embodiment of auxiliary electronics 104 includes a power supply 122, control logic 132, antenna 130 and sensor 134, all or some of which may be disposed on a surface of substrate 146. The power supply 122 includes an energy harvesting antenna 128, charging circuitry 126, and energy storage cells 124. The auxiliary electronics 104 may wirelessly transmit power to the battery 120 of the aIOL 102 by inductively coupling energy harvesting antenna 128 with the energy harvesting antenna 116 of the aIOL 102. Additionally, the auxiliary electronics 104 may wirelessly transmit information detected by the sensor 134 to the aIOL 102 via the antenna 130. The information detected by the sensor may include attempts at accommodation made by the eye in which the ophthalmic device 142 is implanted.

Control logic 132 may include circuit logic that coordinates the operation of other components of auxiliary electronics 104, and may be implemented as hardware logic (e.g., application specific integrated circuit, field programmable gate array, etc.), software/firmware logic executed on a general purpose microcontroller, or a combination of both hardware and software/firmware logic. The control logic 132 may receive ciliary EMG information from the sensor 134 and transmit the information to the aIOL 102 via the antenna 130, for example. Additionally, control logic 132 may control the power supply 122 to cause the power supply 122 is to inductively charge the battery 120 of the aIOL 102. Further, control logic 132 may include communication protocols that govern the transmission and receipt of information from the aIOL 102 via one or more of the antennae 130 and 128.

In the illustrated embodiment of the power supply 122, the energy storage cells 124 power the various embedded electronics, including control logic 132 and sensor 134. The energy storage cells 124 may comprise a plurality of batteries or super capacitors. For example, the energy storage cells 124 may be a plurality of lithium ion or lithium polymer batteries. Energy storage cells 124 may be inductively charged by charging circuitry 126 and energy harvesting antenna 128. Additionally, energy storage cells 124 may provide energy for charging battery 120 of aIOL 102 through inductive coupling. For example, the energy harvesting antennae 128 and 116 may be inductively coupled so that charge from energy storage cells 124 may be wirelessly transmitted to battery 120. Periodically or at times of need, e.g., the battery 120 has low amounts of energy, the control logic 108 may initiate charging of the battery 120 by transmitting a signal indicating such to the control logic 132. In response, the control logic 132 may instruct the power supply 122 to wirelessly charge the battery 120 through inductive coupling.

In one embodiment, antenna 130 and energy harvesting antenna 128 are independent antennae, which serve their respective functions of energy harvesting and communications. In another embodiment, energy harvesting antenna 128 and antenna 130 are the same physical antenna that are time shared for their respective functions of inductive charging and wireless communications with aIOL 102. Additionally or alternatively, power supply 122 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 126 may include a rectifier/regulator to condition the captured energy for charging energy storage cells 124 or directly power control logic 132 without energy storage cells 124. Charging circuitry 126 may also include one or more energy storage devices to mitigate high frequency variations in energy harvesting antenna 128. For example, one or more energy storage devices (e.g., a capacitor, an inductor, etc.) can be connected to function as a low-pass filter.

The sensor 134 may detect ciliary activity to determine when a user's eye is attempting to accommodate and by how much. The ciliary activity information detected by the sensor 134 may be provided to the control logic 132. In some embodiments, the control logic 132 provides the ciliary activity information to the control logic 108 of the aIOL 102 via the antenna 130. The control logic 108 may determine an amount of accommodation based on the ciliary information and cause the dynamic optic 114 to respond accordingly. In such an embodiment, the correlation of the ciliary activity information to an amount of accommodation is performed by the control logic 108 of the aIOL 102. In some embodiments, the correlation of the ciliary EMG information to an accommodation amount may be performed by the control logic 132, and the accommodation amount transmitted to the aIOL 102 by the control logic 132.

Alternatively or additionally, the sensor 134 may monitor movement of the capsular bag. The amount, or relative, movement of the capsular bag may be detected by the sensor 134, which may then be provided to the control logic 132. The control logic 132 may convert the detected movement of the capsular bag into an amount of attempted accommodation, or the detected movement, or a value indicative of the detected movement, may be transmitted to the control logic 108 for conversion. The amount of accommodation may then be provided to the dynamic optic 114.

The external charger 106 may be a loop antenna, e.g., an energy transmitting antenna, for inductively charging the auxiliary electronics 104 and/or the aIOL 102 via connections 140 and 138, respectively. In some embodiments, the external charger 106 may be included in an eye glasses frame that a patient may comfortably wear while charging the auxiliary electronics 104 and/or the aIOL 102. In some embodiments, the external charger 106 may be a wand the user places in close proximity to their eye to inductively charge the auxiliary electronics 104 and/or the aIOL 102.

In operation, the aIOL 102 may provide accommodation to a user via the dynamic optic 114. The aIOL 102, as discussed, may normally operate from energy stored in the battery 120. Occasionally or periodically, however, the battery 120 may be recharged at which time inductive charging of the battery 120 by the auxiliary electronics 104 may occur. The inductive charging may occur based on a schedule and/or based on need. For example, the battery 120 may be charged once or twice a day. Additionally or alternatively, the battery 120 may be charged at the initiation of the logic 108 if energy stored in the battery 120 falls below a minimum threshold.

It is noted that the block diagram shown in FIG. 1 is described in connection with functional modules for convenience in description, but does not necessarily connote physical organization. Rather, embodiments of device 142 may be arranged with one or more of the functional modules ("sub-systems") implemented in a single chip, multiple chips, in one or more integrated circuits, or otherwise.

Figure 2B:
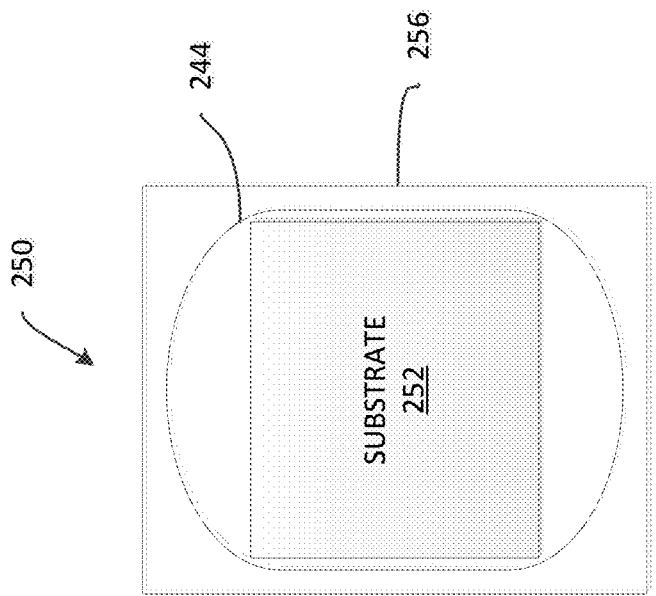
FIG. 2B is an illustrative plan view of auxiliary electronics in accordance with an embodiment of the present disclosure.
Figure 2A:
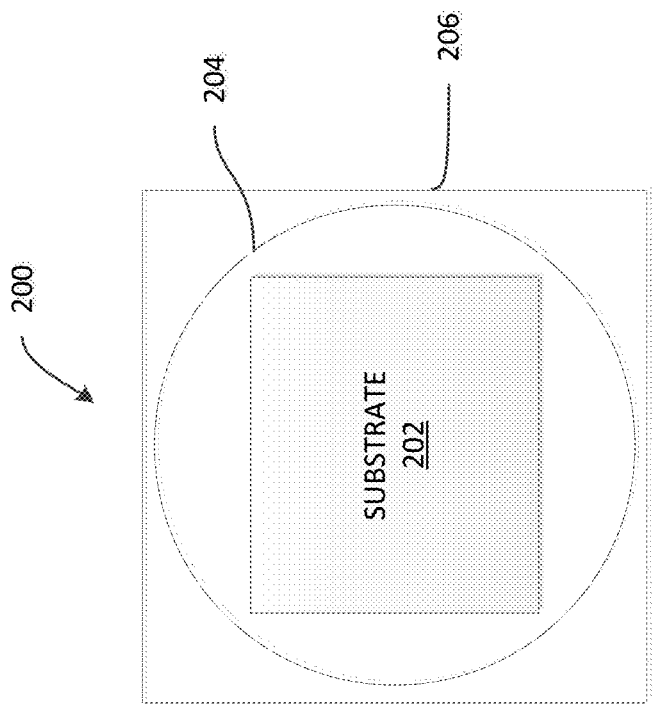
FIG. 2A is an illustrative plan view of auxiliary electronics in accordance with an embodiment of the present disclosure.

FIG. 2A is an illustrative plan view of auxiliary electronics 200 in accordance with an embodiment of the present disclosure. The auxiliary electronics 200 may be an example of the auxiliary electronics 104. The auxiliary electronics 200 may be capable of implantation into an eye. For example, the auxiliary electronics 200 may be at least partially implanted in and/or anchored to the sclera of a user's eye. The auxiliary electronics 200 may at least inductively charge a battery of an accompanying implanted ophthalmic device (not shown), such as an intraocular lens. Additionally or alternatively, the auxiliary electronics 200 may include a sensor capable of detecting ciliary muscle activity through EMG and wirelessly providing the ciliary activity information to the accompanying implanted ophthalmic device. While ciliary activity information is discussed herein, other eye-relative data may be gathered by various sensors, and provided to the accompanying ophthalmic device. In the illustrative embodiment of FIG. 2A, the auxiliary electronics 200 includes a substrate 202, an antenna 204, and an enclosure 206 encapsulating the substrate 202 and antenna 204.

The enclosure 206 may be formed from a biocompatible material enabling implantation into an eye. In some embodiments, the enclosure 206 may hermetically seal the antenna 204 and the substrate 202. For example, the enclosure 206 may be a biocompatible ceramic. Other biocompatible materials, such as biocompatible hydrogel, silicone, hydrophobic acrylic, fluorinated polymethacrylate and/or the like, may also be used to form the enclosure 206. While there are many biocompatible materials that may be used to implement the enclosure 206, the biocompatible material is a non-limiting aspect of the present disclosure and any biocompatible material may be used.

The antenna 204 may be formed into a circle from one or more helical coils. In general, the antenna 204 may be a loop antenna of any shape, such as circular, oval, etc. The antenna 204 may be a conductor formed into a helical loop and capable of being inductively coupled to one or more other antennae. In some embodiments, the antenna 204 may be formed from a wire shaped into one or more helical coils, where the wire may be a metal, e.g., gold, silver, aluminum, etc., or a transparent or semi-transparent conductor, e.g., indium tin oxide. While the antenna 204 is shown as being disposed outside of the substrate 202, the antenna 204 may be disposed on a surface of the substrate 202, such as a backside or front side surface. In some embodiments, the auxiliary electronics 200 may include two physically separate antennae with one antenna providing for energy harvesting and transmission and the other antenna providing for data transmission and receipt. For example, the antenna 204 may include two antennas with one being similar to the energy harvesting antenna 128 and the other being similar to the antenna 130 of the auxiliary electronics 104 of FIG. 1.

Substrate 202 includes one or more surfaces suitable for mounting logic circuits, power supplies, antenna(e), and a sensor. For example, the substrate 202 may be used for the substrate 146 of FIG. 1. Substrate 202 may be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) may be patterned on substrate 202 to form circuitry, electrodes, etc. For example, antenna 204 may be formed by depositing a pattern of gold or another conductive material on substrate 204. Similarly, interconnects between various circuits included on the substrate 202 may be formed by depositing suitable patterns of conductive materials thereon. A combination of resists, masks, and deposition techniques may be employed to pattern materials on substrate 202. Substrate 202 may be a relatively rigid material, such as polyethylene terephthalate ("PET") or another material sufficient to structurally support the circuitry and/or electronics within enclosure 206. Enclosure 206 may alternatively include an arrangement of multiple substrates rather than a single substrate. For example, control logic 132 and power supply 122 may be mounted to one substrate, while antenna 204 and sensor 134 are mounted to another substrate and the two may be electrically connected via interconnects.

Because the auxiliary electronics 200 is intended to be implanted into an eye, size, e.g., volume and area, of the auxiliary electronics 200 may be constrained. However, due to the auxiliary electronics 200 being wirelessly coupled with an accompanying ophthalmic device, there may be more flexibility with regards to its placement location, and therefore its size. For example, if the auxiliary electronics 200 is implanted in or anchored to the sclera, a maximum size of the auxiliary electronics 200 may be greater than if it was implanted in the anterior chamber, for example. An example range of sizes for the auxiliary electronics 200, which may be influenced by the antenna layout, may be from $5.0 \times 5.0 \times 0.4$ mm$^3$ to $5.6 \times 5.6 \times 0.8$ mm$^3$. The enclosure 206 may have a thickness of around 0.1 mm, for example. While battery life is also of concern, the overall size of the auxiliary electronics 200 may allow for larger or more numerous energy storage cells, which may in combination extend the life of a battery included in the auxiliary electronics 200. In some embodiments, the energy storage cells may consume 25% to 50% of the volume of the power source 200.

FIG. 2B is an illustrative plan view of auxiliary electronics 250 in accordance with an embodiment of the present disclosure. The auxiliary electronics 250 includes similar features as the auxiliary electronics 200, such as a substrate 252, antenna 244 and encapsulating material 256. As such, a detailed discussion of the similar features will not be repeated for sake of brevity. Although auxiliary electronics 250 and 200 are alike in various ways, antenna 244 is shown to be in an oval shape, instead of the circular shape of antenna 204. Because a width of the auxiliary electronics 250 may be narrower than a width of the auxiliary electronics 200 due to the oval shape of antenna 244, a smaller incision may be made in an eye in order to implant the auxiliary electronics 250 than may be required to implant the auxiliary electronics 200.

In some embodiments, the auxiliary electronics 200 and 250 may be foldable. Foldability may allow a surgeon to make an even smaller incision in order to implant the power source into the eye. After the power source is inserted through the incision, the power source may be unfolded prior to implanting in or anchoring to the sclera, for example.

Figure 3B:
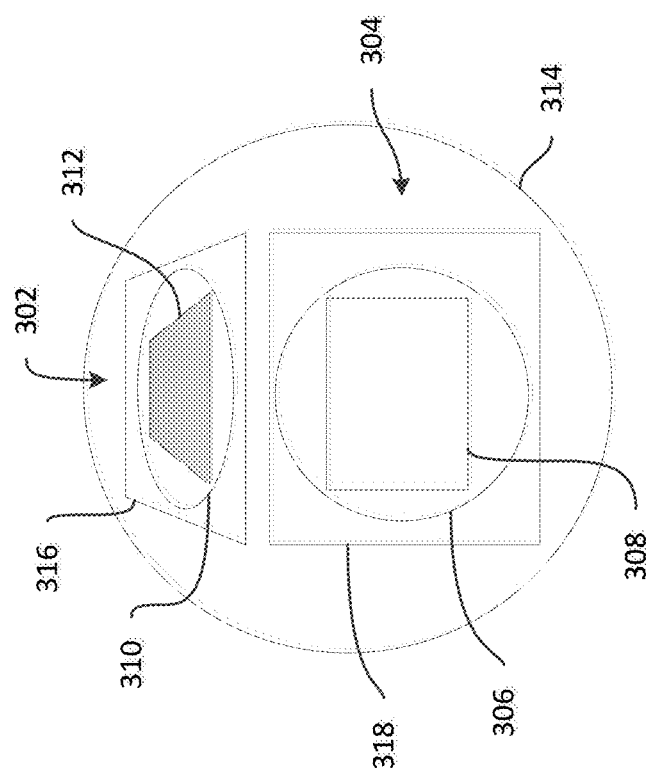
FIG. 3B is an illustrative front view of the ophthalmic device implanted in the eye in accordance with an embodiment of the present disclosure.
Figure 3A:
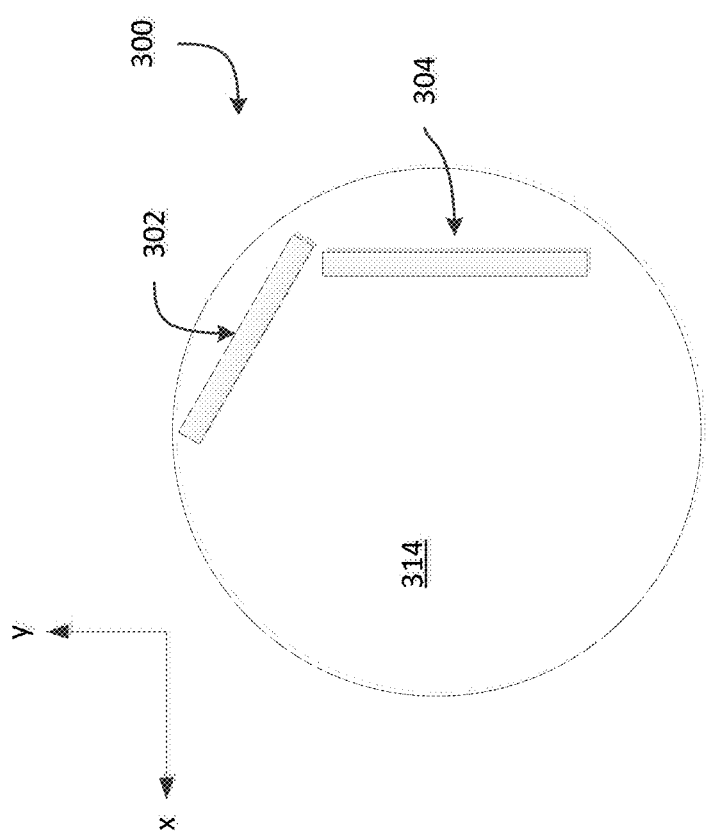
FIG. 3A is an illustrative side view of an ophthalmic device implanted in an eye in accordance with an embodiment of the present disclosure.

FIG. 3A is an example side view of an ophthalmic device 300 implanted in an eye 314 in accordance with an embodiment of the present disclosure. The ophthalmic device may be an example implantation of the ophthalmic device 142 of FIG. 1. The ophthalmic device 300 may include an aIOL 304 and auxiliary electronics 302, which may be implanted in different locations of the eye 314. The aIOL 304 and the auxiliary electronics 302 may be wirelessly coupled for transmission and receipt of energy and data, for example.

The aIOL 304 may be implanted in an eye's anterior chamber, posterior chamber, sulcus, etc., and may be used to provide accommodation to a user. The aIOL 304 may be implanted with an optical axis normal to and in parallel with a visual axis of the eye. For example, a dynamic optic of the aIOL 304 (not shown), may be in the visual axis of the eye 314.

The auxiliary electronics 302 may be implanted in, or partially in, the sclera. Implanting the auxiliary electronics 302 in the scleral may cause the auxiliary electronics 302 to be at an angle with respect to the aIOL 304. The respective angle may be from 48 to 52 degrees, in some embodiments. The auxiliary electronics 302 may also be laterally displaced (in the x direction as shown in FIG. 3A) from the aIOL 304. The lateral displacement may range from 0 to 4 mm, in some embodiments. The respective angle and the lateral displacement between the aIOL 304 and the auxiliary electronics 302 may affect the energy conversion of the inductive energy transfer from the auxiliary electronics 302 to the aIOL 304, in some embodiments.

FIG. 3B is an illustrative front view of the ophthalmic device 300 implanted in the eye 314 in accordance with an embodiment of the present disclosure. The front view of the ophthalmic device 300 shows the various components that may be included in the auxiliary electronics 302 and the aIOL 304. The auxiliary electronics 302, for example, may be an implementation of the auxiliary electronics 104, 200 or 250. Further, the aIOL 304 may be an implementation of the aIOL 102.

The illustrative embodiment of the auxiliary electronics 302 includes a substrate 312, one or more antennae 310, and an enclosure 316. The substrate 312 may include one or more surfaces for disposing electronics thereon, such as control logic, a sensor, and a power supply. In some embodiments, the one or more antennae 310 may be disposed on the substrate 312. The one or more antennae 310 may allow for wireless coupling between the auxiliary electronics 302 and the aIOL 304. The wireless coupling may include both transmission and receipt of data, and inductive charging of one or more batteries, for example. The enclosure 316 may be a biocompatible material that is inert with respect to the eye, and may be (partially) deformable or rigid. In some embodiments, the enclosure 316 may be a biocompatible ceramic that hermetically seals the one or more antennae 310 and the substrate 312.

Similar to the aIOL 102, the illustrative example of the aIOL 304 includes a substrate 308, one or more antennae 306, and an enclosure 318. The one or more antennae 306 may be substantially similar to the one or more antennae 310, and may wirelessly couple the auxiliary electronics 302 and the aIOL 304. The enclosure 318 may be transmissive, e.g., substantially transparent, so that the user may see through it because the aIOL 304 may be in the visual axis of the eye. Further, the substrate 308 may include a dynamic optic, control logic, and a power supply. Because the dynamic optic provides accommodation for the user, the dynamic optic may be centrally located on the substrate 308, and may include actuators for providing the accommodation. The control logic and power supply may be located at an edge of the substrate 308, for example, so not to interfere with a user's vision.

The relative angle and lateral displacement between the auxiliary electronics 302 and the aIOL 304 may be due to various factors of the eye. For example, placing the auxiliary electronics 302 in or on the sclera may cause the relative angle and the lateral displacement with respect to the aIOL 304. Additionally, the size and shape of a user's eye may affect the angle and lateral displacement between the aIOL 304 and the auxiliary electronics 302. As such, the lateral displacement and the relative angle between the components of the ophthalmic device 300 may vary from user to user. In some embodiments, the relative angle and lateral displacement may affect the energy conversion efficiency, which may change from user to user. In some embodiments, the variable in energy conversion may affect the number of times or the length of time a battery of the aIOL 304 may be inductively charged by the auxiliary electronics 302.

While both the relative angle and the lateral displacement may affect the conversion efficiency, a decrease in efficiency due to the lateral displacement may be counteracted by the relative angle. However, in general the smaller the relative angle, the greater the power conversion efficiency. For example, at a lateral displacement of 2 mm and at a relative angle of 48 degrees, the power conversion efficiency using a circular energy harvesting antennae may be greater than 20%.

FIG. 4A is a cross-sectional illustration of an eye 406 with an implanted ophthalmic device 400 including wirelessly coupled structures in accordance with one embodiment of the present disclosure. Ophthalmic device 400 may include some or all of the features of the device 142 for example. In the illustrative embodiment shown, device 400 includes an aIOL 404 wirelessly coupled to auxiliary electronics 402. The particular arrangement of the aIOL 404 and the auxiliary electronics 402 relative to one another is merely illustrative, and not limiting on some embodiments. AIOL 404 is illustrated as being implanted within the posterior chamber 408 behind iris 410. However, aIOL 404 may be implanted into other locations, as well, such as anterior chamber 412 disposed between iris 410 and cornea 414.

The auxiliary electronics 402 is illustrated to be implanted in the sclera 416. In some embodiments, the auxiliary electronics 402 may be at least partially implanted in the sclera under a flap formed in the sclera, as shown in FIG. 4B. Additionally, the auxiliary electronics 402 may be positioned close to ciliary muscle 418 so that an included sensor may detect muscular changes by the ciliary that indicate attempts at accommodation. The cross-sectional illustration of the sclera implant of the auxiliary electronics 402 is shown in FIG. 4B in accordance with an embodiment of the present disclosure. The illustration of FIG. 4B shows the auxiliary electronics 402 placed under a flap 420 formed in the sclera 416. Because the sclera is thin, e.g., around 2 mm in thickness, the formation of the flap may be a delicate procedure and may not fully enclose the auxiliary electronics 402. As such, an alternative, or additional, technique may be used to anchor the auxiliary electronics 402 to the sclera 416 using one or more tabs 422.

FIG. 4C is a cross-sectional view of the auxiliary electronics 402 anchored to the sclera 416 in accordance with an embodiment of the present disclosure. The auxiliary electronics 402 may have one or more tabs 422 formed on or as part of an enclosure. The one or more tabs 422 may be inserted into the sclera 416 to anchor the power source. The auxiliary electronics 402 may be stably held in place by the one or more tabs 422. Anchoring the auxiliary electronics 402 by the tabs 422 may alleviate the need to form the flap 420 in the sclera 416, for example. Additionally, however, implanting the auxiliary electronics 402 may include both the flap 420 and the one or more tabs 422.

FIG. 5 is an example method 500 for wirelessly transmitting power from implanted auxiliary electronics to an implanted aIOL in accordance with the present disclosure. The method 500 may be implemented, for example, by the ophthalmic system 100. In such an example, the aIOL 102 and the auxiliary electronics 104 may be implanted in different locations of a user's eye, and the two components of the system may be capable of wirelessly coupling so that the auxiliary electronics may inductively charge a battery of the aIOL 102. In some embodiments, the auxiliary electronics 104 may be implanted in or anchored to the sclera of the user's eye, whereas the aIOL 102 may be implanted in the anterior chamber, posterior chamber, or capsular bag of the same eye.

The method 500 may begin at block 502 with wirelessly transmitting power by an external charger. The external charger 106 may be an example external charger. In general, the external charger may be external to the user's eye, and placed in proximity to the user's eye to effectuate wireless transmission of power. Block 502 may be followed by block 504, which includes receiving the wirelessly transmitted power by auxiliary electronics to charge an energy storage cell of the auxiliary electronics. The auxiliary electronics may charge one or more energy storage cells included therein using the power wirelessly transmitted by the external charger. The auxiliary electronics and the external charger may use inductive coupling to implement the wireless charging. For example, an antenna of the external charger may be inductively coupled to an antenna of the auxiliary electronics.

Block 504 may be followed by block 506, which includes wirelessly transmitting power by the auxiliary electronics. The auxiliary electronics may include an antenna for wirelessly transmitting the power, which may be the same antenna used for receiving the power from the external charger, and the accommodating intraocular lens may include an antenna for receiving the power. In some embodiments, the power transmitted by the auxiliary electronics may be power stored in an energy storage cell of the auxiliary electronics. Block 509 may be followed by block 508, which includes receiving the wirelessly transmitted power by an accommodating intraocular lens (aIOL). The auxiliary electronics and the aIOL, as discussed, may be amenable to implantation into an eye, and may further be implanted in the same eye of the user. For example, both the auxiliary electronics and the aIOL may be enclosed in a biocompatible material, and the auxiliary electronics may be implanted in, or at least anchored to, the sclera of the user's eye, with the aIOL implanted somewhere in the optical path of the eye to aid in sight.

Lastly, block 508 may be followed by block 510, which includes charging a battery included in the accommodating intraocular lens with the wirelessly transmitted power. The charging of the battery may be performed with the assistance of charge control circuitry, such as the charging circuitry 118. The battery may be periodically charged to ensure the battery of the accommodating intraocular lens is capable of powering electronics and a dynamic optic included therein, for example.

The order in which some or all of the process blocks appear in method 500 should not be deemed limiting. Rather, one of ordinary skill in the art having the benefit of the present disclosure will understand that some of the process blocks may be executed in a variety of orders not illustrated, or even in parallel. For example, blocks 502 and 504 may be performed in parallel with the performance of blocks 506-510. Additionally, some of the blocks may be optional. For example, blocks 502 and 504 may optionally be included in the method 500.

FIG. 6 is an example method 600 for wirelessly transmitting sensor information from implanted auxiliary electronics to an implanted aIOL in accordance with the present disclosure. The method 600 may be implemented, for example, by the ophthalmic system 100. Similar to the method 500, the method 600 may be implemented by the aIOL 102 and the auxiliary electronics 104, which may be implanted in different regions of a user's eye.

The method 600 may begin at block 602 with sensing an attempt at accommodation by a sensor included in auxiliary electronics. The auxiliary electronics, for example, may be implanted in or anchored to a sclera of the user's eye, and include a sensor to detect attempts at accommodation by the user's eye. The sensor, which may be the sensor 134, may detect movements of the ciliary or the capsular bag, for example. The movements may correlate to an amount of accommodation. In some embodiments, the detected movements may be converted into a corresponding amount of accommodation by the auxiliary electronics. The block 602 may be followed by block 604, which includes wirelessly transmitting the sensed attempt of accommodation by the auxiliary electronics. The wireless transmission may include the detected movements (actual or relative), the converted detected movements, or both.

The block 604 may be followed by block 606, which includes receiving the wirelessly transmitted sensed attempt at accommodation by an accommodating intraocular lens (aIOL). The aIOL may receive the sensed attempt, either detected or already converted into an amount of accommodation. If the detected movements are received, control logic of the aIOL, such as control logic 108, may convert the amount or relative amount of detected movement into a correlated amount of accommodation, which may determine an amount of optical power to adjust. The block 606 may be followed by block 608, which may include adjusting an optic included in the accommodating intraocular lens in response to the sensed attempt of accommodation. For example, the control logic 108 of the aIOL 102 may provide control signals to the dynamic optic 114 to cause the dynamic optic 114 to adjust an optical power in order to provide the sensed amount of accommodation.

The order in which some or all of the process blocks appear in method 600 should not be deemed limiting. Rather, one of ordinary skill in the art having the benefit of the present disclosure will understand that some of the process blocks may be executed in a variety of orders not illustrated, or even in parallel.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize. These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device comprising:
   an accommodating intraocular lens (aIOL) enclosed in a first enclosure of a first biocompatible material, the aIOL including:
      a dynamic optic to provide dynamic accommodation to an eye based upon detection of an attempted accommodation by the eye;
      first control logic coupled to the dynamic optic to control actuation of the dynamic optic;
      a battery electrically coupled to power the first control logic and the dynamic optic; and
      a first antenna coupled to the battery; and
   auxiliary electronics enclosed in a second enclosure of a second biocompatible material, the second enclosure discrete and physically separated from the first enclosure, the auxiliary electronics including:
      a second antenna;
      an energy storage cell coupled to the second antenna, the energy storage cell adapted to inductively charge the battery of the aIOL via the second antenna; and
      an accommodation sensor adapted to detect the attempted accommodation of the eye by monitoring a ciliary muscle of the eye or by monitoring movement of a capsular bag of the eye,
      wherein the auxiliary electronics are adapted to wirelessly couple to the aIOL for wireless transmission of power and information indicative of the attempted accommodation by the eye.

2. The ophthalmic device of claim 1, wherein the auxiliary electronics further comprise second control logic, the second control logic electrically coupled to the sensor, and configured to wirelessly transmit a signal indicative of the attempted accommodation to the aIOL.

3. The ophthalmic device of claim 2, wherein the second control logic wirelessly transmits the signal with the second antenna.

4. The ophthalmic device of claim 2, wherein the auxiliary electronics further comprise a third antenna, and wherein the second control logic wirelessly transmits the signal with the third antenna.

5. The ophthalmic device of claim 1, wherein the second biocompatible material hermetically seals the auxiliary electronics.

6. The ophthalmic device of claim 1, wherein the first and second antenna are circular-shaped, helical coil antennae.

7. The ophthalmic device of claim 1, wherein the second antenna is an oval-shaped, helical coil antenna.

8. The ophthalmic device of claim 1, wherein the sensor is adapted to detect the attempted accommodation by monitoring a ciliary muscle of the eye.

9. The ophthalmic device of claim 1, wherein the sensor is adapted to detect the attempted accommodation by monitoring movement of a capsular bag of the eye.

10. The ophthalmic device of claim 1, wherein the sensor is adapted to detect the attempted accommodation by monitoring relative movement of the capsular bag.

* * * * *